United States Patent
Esquivel Bojorquez et al.

(10) Patent No.: US 11,499,969 B2
(45) Date of Patent: Nov. 15, 2022

(54) MULTI-LAYERED BAND AND A METHOD FOR MANUFACTURING A MULTI-LAYERED BAND

(71) Applicants: CONSEJO SUPERIOR DE INVESTIGACIONES CIENTIFICAS, Madrid (ES); INSTITUCIO CATALANA DE RECERCA I ESTUDIS AVANÇATS (ICREA), Barcelona (ES); FUELIUM, SL, Cerdanyola del Valles (ES)

(72) Inventors: Juan Pablo Esquivel Bojorquez, Barcelona (ES); Maria de les Neus Sabate Vizcarra, Barcelona (ES); Marc Castellarnau Aymar, Sabadell (ES); Sergi Gasso Pons, Sant Privat d'en Bas (ES)

( * ) Notice: Subject to any disclaimer, the term of this patent is extended or adjusted under 35 U.S.C. 154(b) by 185 days.

(21) Appl. No.: 17/055,431

(22) PCT Filed: May 13, 2019

(86) PCT No.: PCT/EP2019/062134
§ 371 (c)(1),
(2) Date: Nov. 13, 2020

(87) PCT Pub. No.: WO2019/219563
PCT Pub. Date: Nov. 21, 2019

(65) Prior Publication Data
US 2021/0148902 A1    May 20, 2021

(30) Foreign Application Priority Data
May 14, 2018 (EP) .................................... 18382330

(51) Int. Cl.
*G01N 33/543* (2006.01)
*B01L 3/00* (2006.01)
*G01N 33/558* (2006.01)

(52) U.S. Cl.
CPC ........ *G01N 33/5438* (2013.01); *B01L 3/5023* (2013.01); *G01N 33/558* (2013.01);
(Continued)

(58) Field of Classification Search
CPC .............. G01N 33/5438; G01N 33/558; B01L 3/5023; B01L 2200/12; B01L 2300/0825;
(Continued)

(56) References Cited

U.S. PATENT DOCUMENTS

2006/0137980 A1*  6/2006  Lauks ................... B01L 3/5027
                                                       204/435

OTHER PUBLICATIONS

Gonzalez-Guerrero, et al., Paper-based enzymatic microfluidic fuel cell: From a two-stream flow device to a single-stream lateral flow strip, Elsevier, Journal of Power Sources, vol. 326, Sep. 15, 2016, pp. 410-416.
(Continued)

*Primary Examiner* — Jennifer Wecker
*Assistant Examiner* — Alea N. Martin
(74) *Attorney, Agent, or Firm* — Eugenio J. Torres-Oyola; Victor M. Rodriguez-Reyes; Ferraiuoli LLC

(57) ABSTRACT

A multi-layered band and a method for manufacturing a multi-layered band are disclosed. The multi-layered band comprises a support (1) to hold at least one battery structure (10) formed by overlapped layers including a porous material (11) and two electroactive electrodes (12, 13), one oxidizing (12) and one reducing (13), separated at a certain distance between them and in touch with said porous material (11). The battery structure (10) is configured to be activated upon the addition of a fluid into a given region of
(Continued)

the porous material (11) and to provide electrical energy while said fluid impregnates by capillarity the porous material (11). The overlapped layers are constituted by parallel strips extending longitudinally along the length of the support (1), such that said multi-layered band can be cut transversally providing individual batteries of a same or different width each including the porous material (11) and the electroactive electrodes (12, 13).

15 Claims, 6 Drawing Sheets

(52) U.S. Cl.
CPC ... *B01L 2200/12* (2013.01); *B01L 2300/0825* (2013.01); *B01L 2300/0887* (2013.01); *B01L 2300/12* (2013.01); *B01L 2400/0406* (2013.01)

(58) Field of Classification Search
CPC ......... B01L 2300/0887; B01L 2300/12; B01L 2400/0406
See application file for complete search history.

(56) References Cited

OTHER PUBLICATIONS

Final Report Summary, APPOCS.
Quadrennial Technology Review 2015, Chapter 6: Innovating Clean Energy Techonologies in Advanced Manufacturing, Technology Assessments.
Wing Cheung Mak, et al., Lateral Flow Energy: From Visual to Instrumental, Elsevier, Trends in Analytical Chemistry, vol. 79, May 2016, pp. 297-305.
Esquivel, et al., Microfluidic fuel cells on paper: meeting the power needs of next generation lateral flow devices, The Royal Society of Chemistry, Energy & Environmental Science, Issue 5, 2014, pp. 1744-1749.
Gonzalez-Guerrero, et al., Paper-based microfluidic biofuel cell operating under glucose concentrations within physiological range, Elsevier, Biosensors and Bioelectronics, vol. 90, Apr. 15, 2017, pp. 475-480.
Nguyen, et al., Paper-based batteries: A review, Biosensors & Bioelectronics, Nov. 2013.
High powered thin film batteries for electronics printed on paper in R2R processes, A3Ple, Newsletter #4, Sep. 2014, Project month 40.

\* cited by examiner

MULTI-LAYERED BAND AND A METHOD FOR MANUFACTURING A MULTI-LAYERED BAND

TECHNICAL FIELD

The present invention relates to a multi-layered band providing one or more batteries each formed by different overlapping layers including a porous material and two electroactive electrodes, and to a method for manufacturing said multi-layered band.

BACKGROUND OF THE INVENTION

The most widely used technology for in vitro diagnostics (IVD) is the lateral flow immunoassay. This is mostly because they have a simple test design, they are compact, results are quick and easy to read, and their manufacturing is easy and inexpensive.

The first tests were made for the detection of human chorionic gonadotropin (hCG), as pregnancy test. Today, there are commercially available tests for monitoring ovulation, detecting infectious disease organisms, analyzing drugs of abuse, and measuring other analytes important to human physiology. Products have also been introduced for veterinary testing, agricultural applications, environmental testing, and product quality evaluation. FIG. 1 of the attached drawings shows a typical configuration of a lateral flow test.

A lateral flow assay consists of different overlapped porous membranes placed over a flat substrate (backing). The sample is added on the sample pad and flows by capillarity towards the wick or absorbent pad. The conjugate pad contains colored particles conjugated with an antigen or antibody, these particles are re-dissolved with the sample and flow together to the nitrocellulose membrane. The nitrocellulose contains two regions onto which other specific biological components have been immobilized. These are typically proteins, either antibody or antigen, which have been laid down in bands in specific areas of the membrane where they serve to capture the analyte and the conjugate as they flow over the capture lines. Excess reagents move past the capture lines and are entrapped in the wick or absorbent pad. Results are interpreted on the reaction zone in the nitrocellulose membrane as the presence or absence of lines (test line and control line), these can be read either by eye or using an electronic reader.

The different porous membranes comprising the lateral flow are assembled over a backing material coated with a pressure sensitive adhesive (PSA) (FIG. 2). The backing materials are typically cardboard, polystyrene or other plastic materials coated with a medium to high tack adhesive. The backing comes with a protective release liner, which is removed prior to lamination. This release liner can be kiss cut to allow the sequential removal of selected parts for lamination. The use of backing material provides rigidity and ease of handling to a lateral flow immunoassay strip and is a necessity in order to laminate multiple materials. The lamination process allows the alignment and overlapping of the multiple materials with acceptable tolerances.

Lamination of lateral flow components can be done by two methods, batch mode or in continuous in-line or reel-to-reel mode. In batch processing, card lengths of materials are processed individually, assembled into cards, and cut into strips. These backing cards usually have a length of 30 to 60 cm and include a series of peel-off covers to be removed to attach the various components. Batch lamination can be done by hand or using a laminator. The laminator helps placing the components and ensures a reproducible assembly.

In-line or reel-to-reel processing, all components are maintained in roll format until they have been treated and laminated, and only then are they cut into either individual strip or card lengths for final packaging.

Once the assembly is laminated, the master card or roll is cut in individual test strips. There are three typical types of cutters: guillotine, single rotary blade, and rotary card cutter. Test strips are usually cut to widths of 3 to 6 mm.

After cutting, the strips can be placed inside a plastic box or cassette that provides a sample container, a buffer inlet if needed and a window to see the results area on the nitrocellulose strip. These cassettes can hold one or multiple test strips inside.

Apart from that, although lateral flow assays do not require any electric power to operate (they rely on capillary forces and the results can be read by the naked eye), their performance can be improved by the use of electrical elements or instrumentation providing electronic readers. These electronic readers may perform a variety of functions including, for example, sample pretreatment, hydraulic controls, heating, timing, light sources, photodetectors, RF communications and, in most cases, screens as the interface between the device and the user to set up the test and display the result. The use of an electronic reader has the advantage of providing an unambiguous qualitative/quantitative result of an assay and can improve the sensitivity and limit of detection. Either benchtop equipment or portable handheld devices, electronic instrumentation requires a source of electrical power in order to perform their functions. In portable readers the power demand has been fulfilled with either primary or secondary batteries.

Some products in the market offer disposable digital pregnancy or ovulation tests that rely on button-cell batteries to perform an optical measurement and yield semiquantitative results. After a single use (or a few uses in the case of ovulation tests), the whole device is thrown away. This includes the lateral flow strip, the plastic casing, the optical sensor, an LCD display, electronic components mounted on a PCB, and the almost fully charged battery.

Also, document "*Paper-based enzymatic microfluidic fuel cell: From a two-stream flow device to a single-stream lateral flow strip*", González-Guerrero Maria José et al. presents a first approach towards the development of a cost-effective enzymatic paper-based glucose/$O_2$ microfluidic fuel cell in which fluid transport is based on capillary action. A first fuel cell configuration consists of a Y-shaped paper device with the fuel and the oxidant flowing in parallel over carbon paper electrodes modified with bioelectrocatalytic enzymes. The anode consists of a ferrocenium-based polyethyleneimine polymer linked to glucose oxidase (GOx/Fc-C6-LPEI), while the cathode contains a mixture of laccase, anthracene-modified multiwall carbon nanotubes, and tetrabutylammonium bromide-modified Nafion (MWCNTs/laccase/TBAB-Nafion). In the configuration proposed by this prior art document, see FIG. 3A, the electrodes are coplanar and facing each other perpendicular to the strip of paper through which flows the liquid that will activate the fuel cell.

"*Microfluidic fuel cells on paper: meeting the power needs of next generation lateral flow devices*", J. P. Esquivel et al. presents the development of microfluidic fuel cells as paper-based power sources in a standard lateral flow test format. These fuel cells benefit from the laminar flow occurring in a porous material by capillarity to separately react with two parallel streams, anolyte and catholyte, without an ionic exchange membrane or external pumps. This microfluidic fuel cell approach enables a more straightforward integration with typical lateral flow test strips and a cost-effective manufacturing. In the configuration proposed by this prior art document, see FIG. 3B, the electrodes are arranged at different levels, separated by the paper strip.

"*Paper-based microfluidic biofuel cell operating under glucose concentrations within physiological range*", González-Guerrero Maria José et al. addresses the development of a compact paper-based enzymatic microfluidic glucose/$O_2$ fuel cell that can operate using a very limited sample volume (≈35 μl) and explores the energy generated by glucose at concentrations typically found in blood samples at physiological conditions (pH 7.4). Carbon paper electrodes combined with a paper sample absorption substrate all contained within a plastic microfluidic casing are used to construct the paper-based fuel cell. In the configuration proposed by this document, the electrodes are also arranged at different levels, separated by the paper strip (see FIG. 3C).

In any of the above-cited documents, the electrical contacts with the electrodes are lateral and protrude outside the dimension of the strip of paper that constitutes the fluidic of the battery or fuel cell. Moreover, the electrodes do not have continuity along all the surface of the strip of paper. Therefore, the arrangement of the electrodes in the quoted prior art complicates the design and the capacity to be integrated in line in band or roll format.

Apart from that, *Final Report Summary—APPOCS (Autonomous Paper-based Point-of-Care Biosensing System)* discloses the development of paper-based fuel cells, batteries and redox flow batteries to power point-of-care analytical devices. The devices allow the autonomous quantitative measurement of a biological sample and visualize the results within a thin, flexible and disposable package. The document discloses that the paper-based batteries can be fabricated with roll-to-roll processing, but it do not provide any details on the in line implementation in band or roll format.

Roll to Roll Processing, "*Technology Assessments*" makes reference to roll-to-roll manufacturing techniques but not to lateral flow. Throughout the document it is mentioned that battery components (membranes, electrodes, etc.) can be manufactured by roll-to-roll, but this document does not make reference to a whole battery manufactured by said manufacturing technique. Although Lithium batteries and printed batteries are acknowledged, these are a type of batteries that carry the electrolyte encapsulated (sealed), therefore have to be custom made designs and do not have the possibility to be cut in different sizes after the assembly or lamination of the different components/layers.

"*Lateral-flow technology: From visual to instrumental*", Cheung Mak et al. discloses the manufacture of lateral flow test strips. The document examines recent labelling strategies, the relative merits of optical and electrochemical transducers and explores the evolution of recognition elements that are now being incorporated into these systems.

Despite the known solutions in the field, there are not known multi-layered bands integrating one or more batteries, with a same or different width and performance (capacity or power), which are fabricated using the same materials and manufacturing methods used in the lateral flow test industry and that can also integrate/include a lateral flow assay. None of the known solutions present a battery system that can be fabricated in band or a roll format, where every individual cut along the band or roll dimension, constitutes a battery unit, independently of the cutting.

DESCRIPTION OF THE INVENTION

In accordance with the present disclosure, provided is, according to a first aspect, a multi-layered band, provided in a card-length format or in a roll format, and comprising a support to hold a battery structure (it can hold more than one) formed by a plurality of overlapped layers including a porous material and at least two electroactive electrodes, one oxidizing electrode and one reducing electrode.

The electroactive electrodes are separated at a certain distance between them and are in touch with the porous material. Besides, the battery structure is configured to be activated upon the addition of a fluid, acting as the battery electrolyte, into a given region of the porous material and to provide electrical energy while said fluid impregnates by capillarity the porous material.

The cited overlapped layers are constituted by parallel strips extending longitudinally along the length of the support (for example a flat surface or backing card), such that the multi-layered band can be cut transversally then providing individual batteries of a same or different width depending on the cut configuration. Thus, depending on the size of each individual battery each will have a given electrical power because of the size and configuration of the electroactive electrodes involved.

The proposed multilayered design simplifies the manufacture and allows the multilayered band to be integrated in band or roll format because the electrodes extend and can be contacted within the same longitudinal dimension of the porous material that serves as the battery body. This arrangement of the electrodes together with the fact that the battery does not contain any electrolyte also gives the freedom to cut the batteries to any width, allowing to easily changing the capacity or power that the battery can supply.

In an embodiment, the proposed multi-layered band also integrates a lateral flow assay device formed by different overlapped porous membranes assembled over the support. For example, the lateral flow assay device can be arranged interconnected to the battery structure either fluidically, electrically or both.

Preferably, the battery structure comprises a paper-based battery. In this case, the oxidizing electrode can comprise redox species, carbon, metals, alloys or polymers, and the reducing electrode can comprise an air-breathing cathode, redox species, carbon, metals, alloys or polymers.

In an embodiment, the oxidizing electrode and the reducing electrode of the battery structure are arranged side by side. Alternatively, in another embodiment, the electroactive electrodes are arranged face to face.

In case of the support holding several battery structures these can be connected in series to increase an output voltage or in parallel to increase an output current.

Moreover, the oxidizing electrode and the reducing electrode can be in touch with the porous material using mechanical fixing means (such as pins, cables, etc.), by a welding spot, or by using an attaching agent either electrically conductive or not such as an adhesive or a polymer coating. If a conductive adhesive or polymer coating is used this provides electrical connection between the electroactive electrodes.

Besides, the attaching agent can be a porous film or a perforated film in at least some parts to provide permeation of oxygen to at least the reducing electrode.

In an embodiment, the proposed multi-layered band also includes a series of longitudinal pre-cuts passing through the multi-layered band. The series of longitudinal pre-cuts can be spaced apart at an equal or different distance between them, such that the cut individual batteries can all be of the same width or different width.

Embodiments of the present invention also provide according to a second aspect a method for manufacturing a multi-layered band, by assembling a plurality of layers including a porous material and at least two electroactive electrodes, one oxidizing and one reducing, over a support forming a multi-layered band; and cutting the multi-layered band transversally generating multiple batteries of a same or different width each including the porous material and the at least two electroactive electrodes.

According to the proposed method, the plurality of layers are constituted by parallel strips extending longitudinally along the length of the support. Moreover, the two electroactive electrodes are separated at a certain distance between them and are in touch with the porous material, and the plurality of layers form at least one battery structure that is activated upon the addition of a fluid into a given region of the porous material providing electrical energy while said fluid impregnates by capillarity the porous material.

The proposed method can be implemented via batch or reel-to-reel processing methods.

In an embodiment, different porous membranes forming a lateral flow assay device are also assembled over the support.

BRIEF DESCRIPTION OF THE DRAWINGS

The previous and other advantages and features will be more fully understood from the following detailed description of embodiments, with reference to the attached figures, which must be considered in an illustrative and non-limiting manner, in which.

DETAILED DESCRIPTION OF PREFERRED EMBODIMENTS

The present invention provides a multi-layered band that comprises at least one battery structure 10 (preferably a paper-based battery) that is composed of a porous material or membrane 11 in contact with at least two electroactive electrodes 12, 13 in a film format, at least one of them oxidizing (anode) 12 and at least one of them reducing (cathode) 13.

Figure 7:
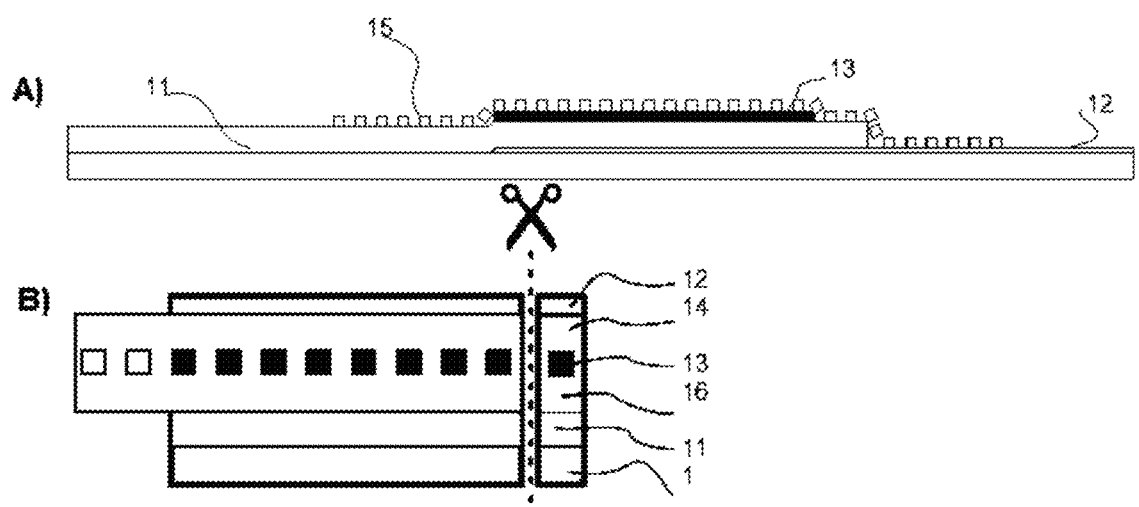
FIG. 7 shows an example of the attaching agents to cover reducing electrode. A) Side-view of battery using porous attaching agent. B) Top-view of battery using attaching agent with periodic openings/apertures.

According to a preferred embodiment, the proposed multi-layered band also comprises a lateral flow assay device 20 (see FIG. 7) formed by different overlapped porous membranes assembled over the support 1.

The porous material 11 can be composed of any porous material capable of wicking a liquid or fluid by capillarity, such as cellulose, nitrocellulose, glass fiber, polymer, fabric, etc. The oxidizing electrode 12 can be composed of any redox species, metal, alloy or polymer oxidizing material, for example of anthraquinone, viologen, TEMPO, Calcium, Iron, Sodium, Potassium, Magnesium, Zinc, Aluminum, among others. The reducing electrode 13 can be composed of any redox species, metal, alloy or polymer reducing material, for example of an air-breathing cathode, Manganese, Iron, Cobalt, Nickel, benzoquinone, TEMPO, among others. That is, in this case the battery 10 generates energy from the oxidation of the anode 12 and a reduction reaction at the cathode 13.

The reaction of the battery 10 is triggered by the addition of a liquid or fluid into the porous material 11. The fluid would act as the battery electrolyte that conducts the ions to close the battery electrochemical reaction. A solid or gel compound can be dry-stored within the porous material 11 to increase the ionic conductivity between the electroactive electrodes 12, 13. The stored electrolyte can be dissolved or re-hydrated upon the addition of the fluid to the porous material 11.

The battery 10 can provide an output power with a stagnant electrolyte, although a flowing electrolyte would result in a high power output. The electrolyte can flow by capillary action and the flow rate can be sustained as long as the porous material 11 continues wicking or the porous material 11 is put in contact with an additional porous material that acts as an absorbent pad.

The battery 10 decreases its performance as the electroactive electrodes 12, 13 are consumed and its reaction stops when at least one of the electroactive electrodes 12, 13 is completely consumed.

The electrodes active area and shape determine the current provided by the battery 10. The electrode thickness has an effect in the duration of the battery 10 in operation and the internal resistance of the battery 10.

Figure 1:
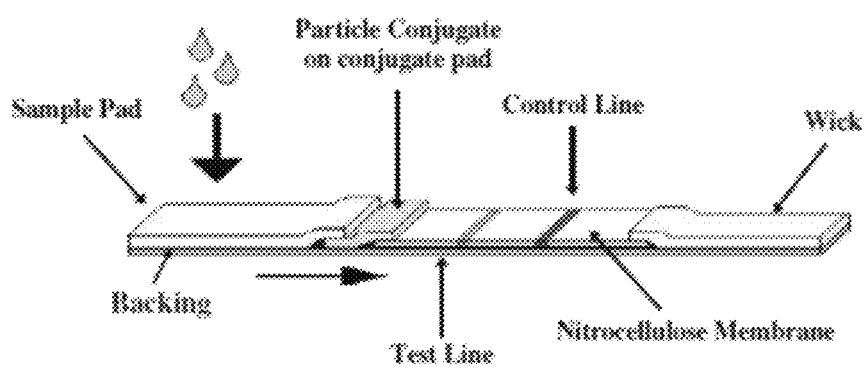
FIG. 1 is a schematic view of a lateral flow test strip according to the state of the art.
Figure 2:
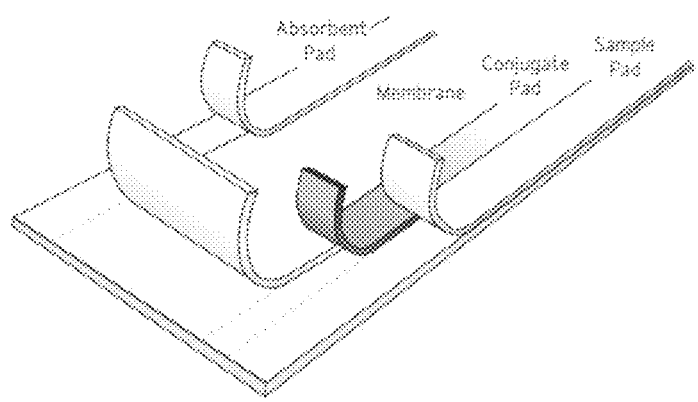
FIG. 2 is a schematic illustration of the lamination of materials for lateral flow fabrication as per the state of the art.
Figure 3A:
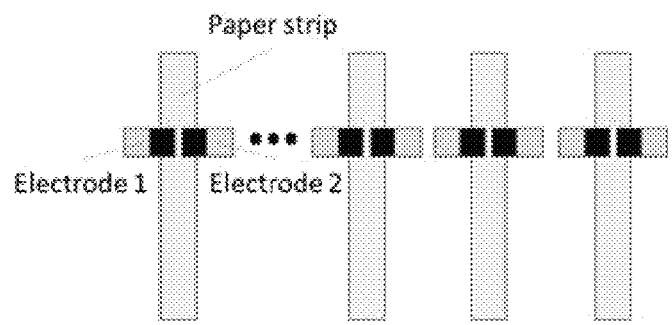
FIGS. 3A to 3C represent different schematic illustrations of the electrodes arrangement in prior art paper battery configurations.
Figure 3B:
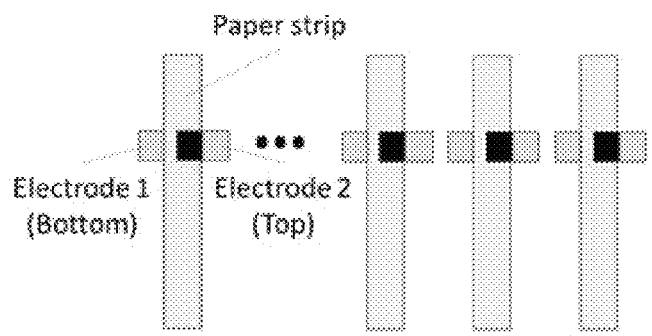
Figure 3C:
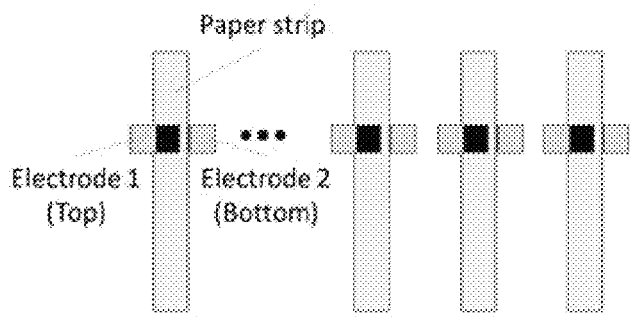
Figure 4:
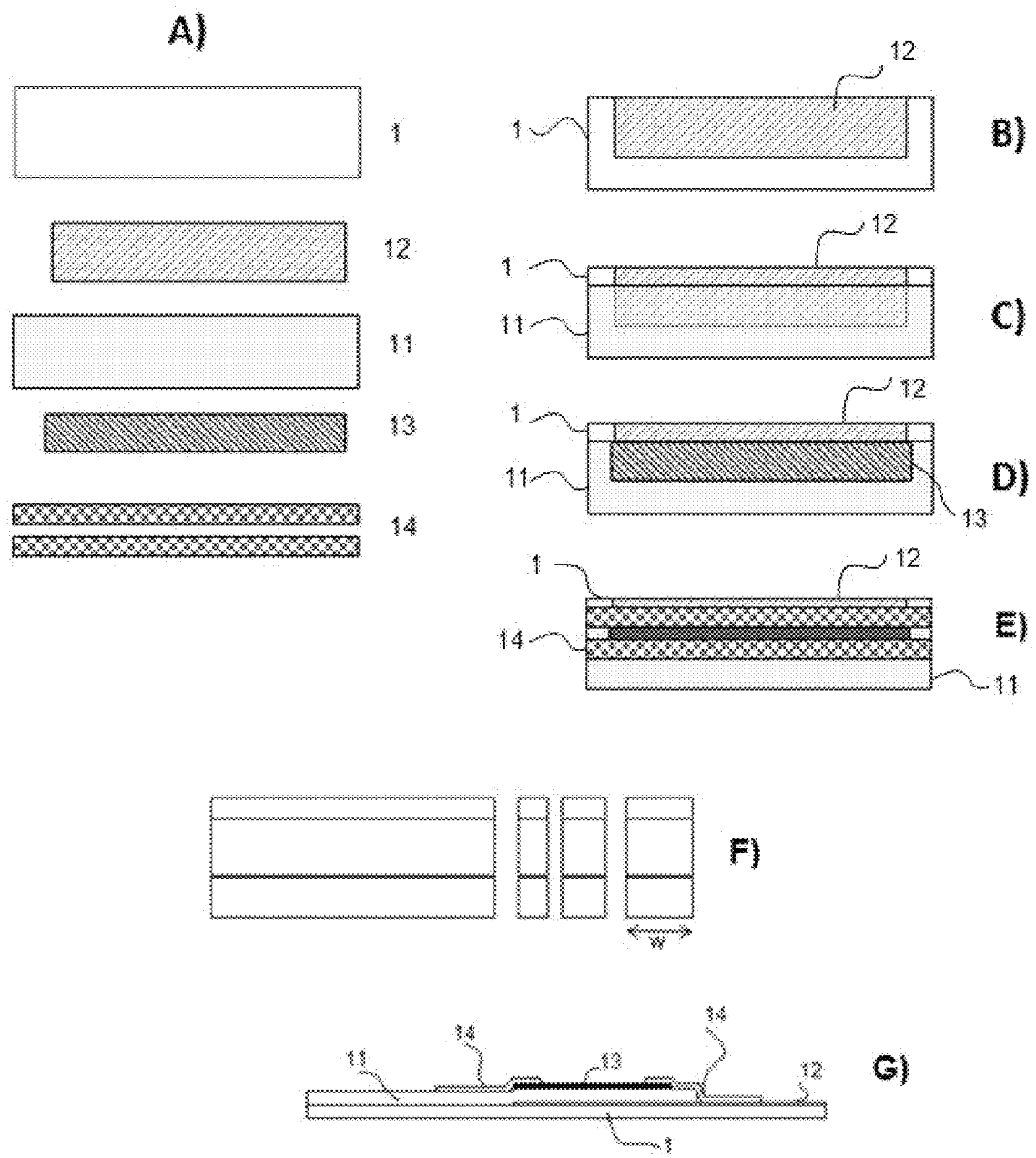
FIG. 4 shows an example of fabrication of one of the batteries that are included in the proposed multi-layered band. A) Materials. B-E) Lamination of different layers for battery construction. F) Cutting of individual batteries of different widths. G) Cross-section view of battery.
Figure 5:
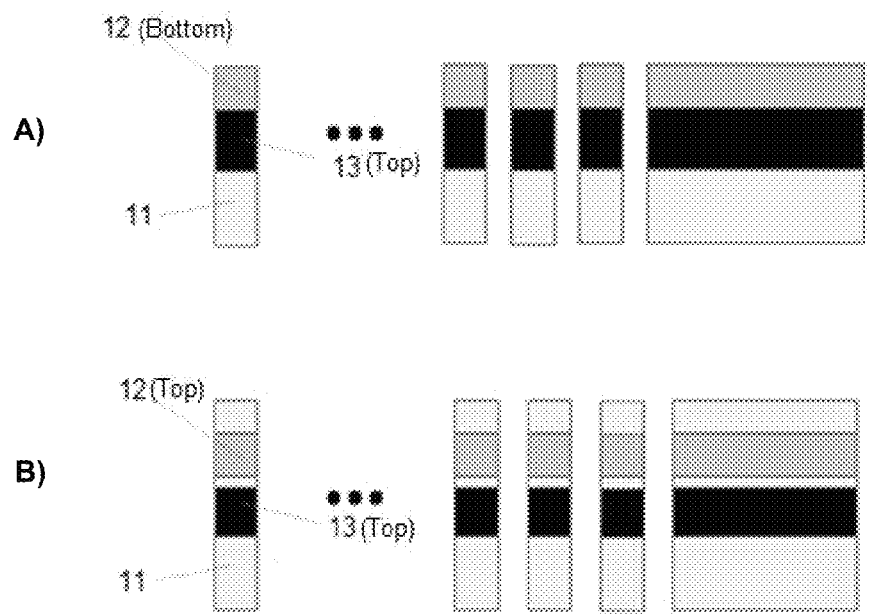
FIG. 5 shows examples of the laminated format of the proposed multi-layered band; A) illustrates a sandwich or superposed configuration and B) illustrates side-by-side configuration.

With reference to FIG. 4, therein it is illustrated an embodiment of the fabrication of the battery 10. As shown in the figure, the battery 10 is fabricated following the same strategies and processes of a lateral flow assay, i.e. assembling different layers on a substrate 1 and then cutting them transversally to generate multiple individual batteries.

Several configurations are possible to mount the battery 10 with respect to lateral flow assay 20. Following table describes the pros and cons of each configuration.

TABLE 1

Examples of battery configurations in relation to the assay

| Position of battery in the assay | PROS | CONS |
|---|---|---|
| Sample pad | Energy from the battery is produced from the moment the sample is added. | The by-products of the battery reaction might affect the operation of the assay. |
| Sink pad | By-products of battery reaction do not affect the assay. The battery can provide a signal of the moment when the liquid sample has reached the pad. Easy to include in the assay. | The flow rate of sample in the battery and the filling time is limited by the assay membrane materials. |
| Backside | Does not interfere with the assay. It can be fabricated independently of the assay and combined during final assembly. The battery can take advantage of the whole length of the assay. | It may be more expensive to integrate. |
| Parallel | Battery is fabricated completely independent from the assay. The battery can be fabricated with less design restrictions. | The battery has to be connected to the assay afterwards which may lead to higher production costs. |

Depending on the desired configuration and/or application, the battery 10 (or batteries) can be laminated at the same time of the lateral flow assay 20 or produced separately and "placed together" afterwards.

The paper used in the battery 10 can be used as any of the components in the lateral flow test assay 20, for example sample pad, sink pad, conjugate pad or the membrane. The position of the battery 10 with respect to the assay would determine the size, shape and assembly order of the materials used for lamination.

The electroactive electrodes 12, 13 can be placed in a coplanar configuration (side by side) or in vertical configuration (face to face with paper in-between). The electroactive electrode 12, 13 configuration and the separation between electrodes 12, 13 determine the internal resistance of the battery 10 and hence the response of the battery 10.

Figure 6:
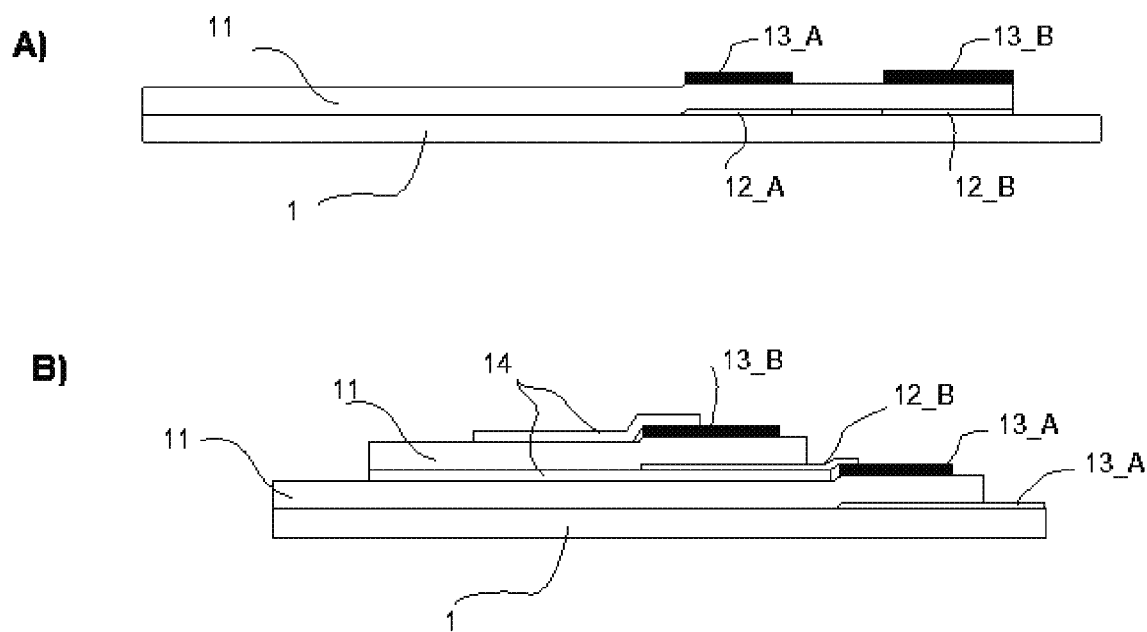
FIG. 6 shows some battery stack configurations according to different embodiments of the present invention; A) illustrates a 2-battery stack with single paper strip and B) a 2-battery stack with separated paper strip for each battery.

Moreover, in present invention several batteries 10 can be connected in series to increase the output voltage or in parallel to increase the output current, as shown in FIG. 6. The battery stack can be implemented in the same porous material 11 or in separated segments of porous material. The connection between the different electroactive electrodes 12_A, 13_A, 12_B, 13_B composing the battery stack can be done internally during fabrication or can be done externally by means of cables, pins, a welding spot, (conductive) adhesives or pastes, etc.

Besides, the attaching agent 14 used to laminate the battery 10 can be provided with a conductive layer such as a conductive adhesive, a conductive polymer coating, metal evaporation or sputtering or by printing patterns by printing electronics techniques. This attaching agent 14 can be used to contact the electroactive electrodes 12, 13 while fixing the components of the lamination.

In a particular embodiment, the attaching agent 14 comprises a pressure sensitive adhesive (PSA).

The attaching agent 14 covering the battery 10 can be a porous film 15 (FIG. 7A) or a film with (periodical) openings/apertures (FIG. 7B), at least in some of its parts, to allow permeation of oxygen to the cathode electrode 13.

Figure 8:
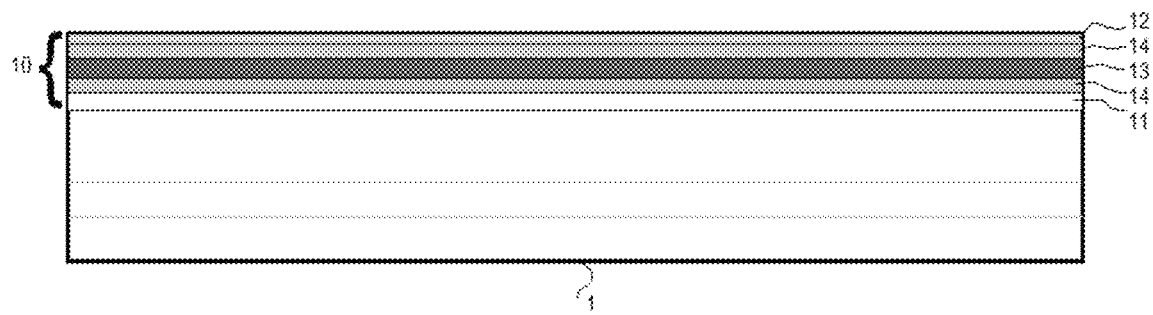
FIG. 8 shows an example of backing card including laminated battery.

With reference to FIG. 8, therein it is illustrated an embodiment of the proposed multi-layered band fabrication using batch method by pre-assembling the battery 10 in a backing card acting as support 1. The backing card 1 can leave spaces available to assemble the lateral flow assay 20 components such as the nitrocellulose membrane 22, conjugate 23 and other pads 24.

Figure 9:
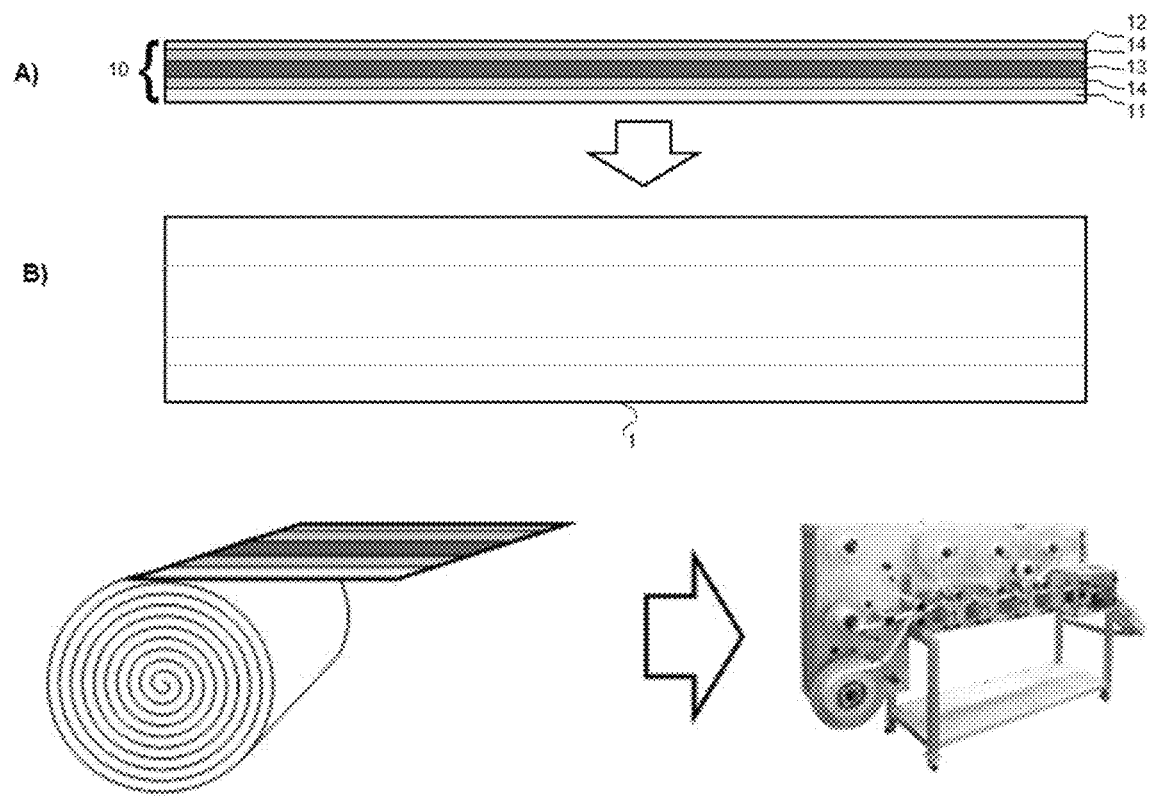
FIG. 9 shows examples of battery lamination with assay in (A) batch and (B) reel-to-reel methods.

In another embodiment, referring to FIG. 9, the battery 10 can be pre-assembled in a card-length format (FIG. 9A) to be assembled in a backing card 1 with the assay 20 in batch mode or in a roll format (FIG. 9B) to be laminated in reel-to-reel processing.

Figure 10:
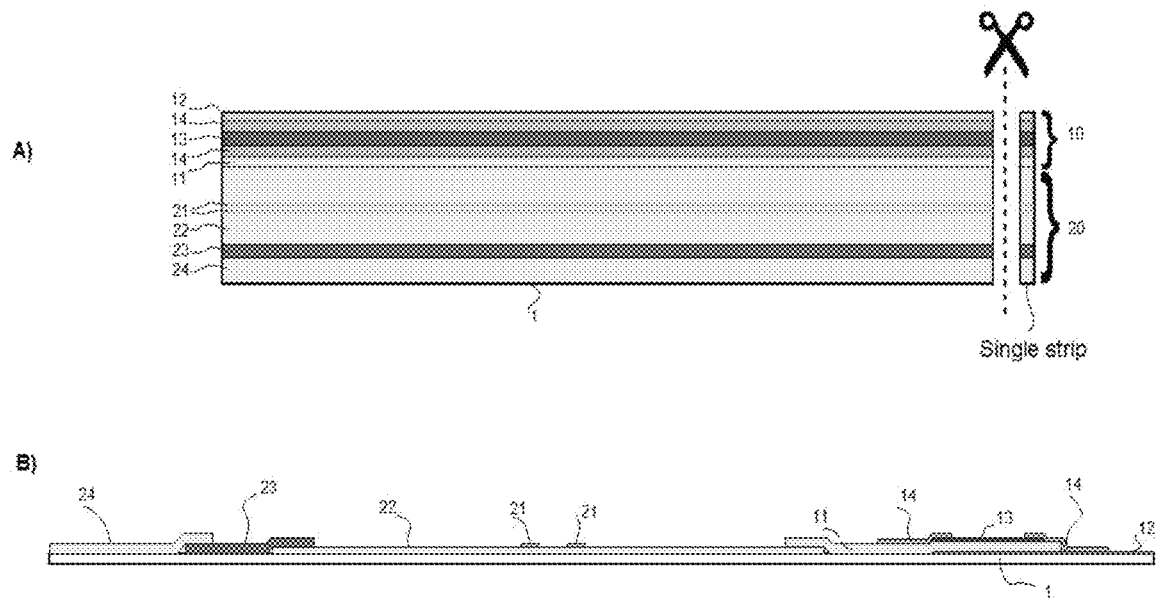
FIG. 10 schematically shows an example of backing card including battery and assay. A) Top view of assembled backing card. After assembly, the backing card is cut in single strips. B) Cross-section view of assay and battery.

After assembly of the different laminate materials on the backing substrate 1, the card is cut in individual strips of the desired width w. FIG. 10 shows top and cross sectional views of an example of assembled backing card with the main lateral flow assay 20 components (sample pad 24, conjugate pad 23, nitrocellulose membrane 22 with dispensed test and control lines 21) in which the battery paper strip 11 acts as the assay absorbent pad.

In yet another embodiment, in this case not illustrated, the cut single strip which includes the battery/batteries 10 and optionally the lateral flow assay 20 is arranged inside a casing or cassette, to provide robustness and facilitate addition of the liquid or fluid sample and reading of the result. The casing can be made of plastic or other materials such as a polymeric material or a wax. The casing can incorporate other components, such a conducting track, an electrical discharge load, a lighting unit such as a LED, etc.

It should be apparent to those skilled in the art that the description and figures are merely illustrative and not limiting. They are presented by way of example only.

The scope of the present invention is defined in the following set of claims.

What is claimed is:

1. A multi-layered band, comprising:
   a support configured to hold at least one battery structure formed by a plurality of overlapped layers, said plurality of overlapped layers including:
   a porous material, and
   at least two electroactive electrodes, one oxidizing electrode and one reducing electrode,
   the electroactive electrodes being separated at a certain distance between them and in touch with said porous material, the battery structure being configured to be activated upon the addition of a fluid, acting as the battery electrolyte, into a given region of the porous material and to provide electrical energy while said fluid impregnates by capillarity the porous material, wherein said overlapped layers are constituted by parallel strips extending longitudinally along the length of the support, such that said multi-layered band can be cut transversally providing individual batteries of a same or different width each including the porous material and the at least two electroactive electrodes.

2. The band of claim 1, further comprising a lateral flow assay device formed by different overlapped porous membranes assembled over the support.

3. The band according to claim 2, wherein the lateral flow assay device is arranged interconnected with the battery structure.

4. The band according to claim 1, wherein the battery structure is a paper-based battery, wherein the oxidizing electrode comprises redox species, carbon, metals, alloys or polymers, and wherein the reducing electrode comprises an air-breathing cathode, redox species, carbon, metals, alloys or polymers.

5. The band according to claim 1, wherein the oxidizing electrode and the reducing electrode of the battery structure are arranged side by side or face to face.

6. The band according to claim 1, wherein the support comprises several battery structures connected in series to increase an output voltage or in parallel to increase an output current.

7. The band according to claim 1, wherein the oxidizing electrode and the reducing electrode are in touch with the porous material using a mechanical fixing element or using an attaching agent including an adhesive, a polymer coating or an adhesive or polymer coating that is electrically conductive at least in part.

8. The band according to claim 7, wherein the attaching agent is porous or perforated in at least some parts to provide permeation of oxygen to at least the reducing electrode.

9. The band according to claim 1, further comprising a series of longitudinal pre-cuts passing through the multi-layered band, said series of longitudinal pre-cuts being spaced apart at an equal or different distance between them, such that the cut individual batteries can all be of the same width or different width.

10. The band according to claim 1, comprising a card-length format or a roll format.

11. A method for manufacturing a multi-layered band, the method comprising:
    assembling a plurality of layers including a porous material and at least two electroactive electrodes, one oxidizing and one reducing, over a support forming a multi-layered band,
    said plurality of layers being constituted by parallel strips extending longitudinally along the length of the support,
    said at least two electroactive electrodes being separated at a certain distance between them and being in touch with said porous material, and
    said plurality of layers forming at least one battery structure that is activated upon the addition of a fluid, acting as the battery electrolyte, into a given region of the porous material providing electrical energy while said fluid impregnates by capillarity the porous material; and
    cutting the multi-layered band transversally generating multiple batteries of a same or different width each including the porous material and the at least two electroactive electrodes.

12. The method of claim 11, further comprising assembling different porous membranes forming a lateral flow assay device over the support.

13. The method of claim 11, wherein the assembling is performed via a batch processing method or a reel-to-reel processing method.

14. The method of claims 11, wherein the oxidizing electrode and the reducing electrode are arranged side by side or face to face.

15. The method of claim 11, wherein said cutting is performed using a series of longitudinal pre-cuts passing through the multi-layered band, said series of longitudinal pre-cuts being spaced apart at an equal or different distance between them.

* * * * *